US012458561B2

(12) United States Patent
Cavalletti

(10) Patent No.: US 12,458,561 B2
(45) Date of Patent: Nov. 4, 2025

(54) INTEGRATED DEVICE FOR THE NON-INVASIVE PERSONALISED TREATMENT OF SKIN BLEMISHES AND ASSOCIATED MULTI-STEP METHOD

(71) Applicant: FENIX GROUP S.R.L., Montesilvano (IT)

(72) Inventor: Gianluca Cavalletti, Montesilvano (IT)

(73) Assignee: FENIX GROUP S.R.L., Montesilvano (IT)

(*) Notice: Subject to any disclaimer, the term of this patent is extended or adjusted under 35 U.S.C. 154(b) by 1146 days.

(21) Appl. No.: 17/422,895

(22) PCT Filed: Jan. 13, 2020

(86) PCT No.: PCT/IB2020/050221
§ 371 (c)(1),
(2) Date: Jul. 14, 2021

(87) PCT Pub. No.: WO2020/148624
PCT Pub. Date: Jul. 23, 2020

(65) Prior Publication Data

US 2022/0062095 A1 Mar. 3, 2022

(30) Foreign Application Priority Data

Jan. 16, 2019 (IT) ........................ 102019000000679

(51) Int. Cl.
*A61H 15/00* (2006.01)
*A61B 17/32* (2006.01)
(Continued)

(52) U.S. Cl.
CPC ..... *A61H 15/02* (2013.01); *A61B 17/320068* (2013.01); *A61H 9/0057* (2013.01);
(Continued)

(58) Field of Classification Search
CPC ... A61H 15/0085; A61H 15/0092; A61H 9/00
See application file for complete search history.

(56) References Cited

U.S. PATENT DOCUMENTS 3,934,579 A * 1/1976 Brodbeck .......... A61H 15/0092 601/123
5,685,827 A 11/1997 Shimizu
(Continued)

FOREIGN PATENT DOCUMENTS

CN 106 038 208 10/2016
EP 1 844 750 A1 10/2007
(Continued)

OTHER PUBLICATIONS

International Search Report for PCT/IB2020/050221 dated Mar. 13, 2020, 5 pages.
(Continued)

*Primary Examiner* — LaToya M Louis
(74) *Attorney, Agent, or Firm* — NIXON & VANDERHYE

(57) ABSTRACT

Integrated device for the non-invasive personalised treatment of skin blemishes includes: a handpiece for performing a percussive treatment on the body/face, causing a microtrauma on the wrinkle furrow, facilitating the natural recovery and the reduction of the wrinkle depth; a handpiece for carrying out an ablative micro-vibration treatment on the body, suitable to expand or compact the cutaneous tissue by alleviating wrinkles, stretch marks and scars with an exfoliating effect; a handpiece for performing a compressive micro-vibration treatment on the face, expanding the pores of the epidermis; a device for adjusting the rotation and vibration of the handpieces; an electric energy absorption sensor for each handpiece, communicating the detected data to a control unit which acts on the frequency adjustment devices obtaining a variation in the rotation and vibration
(Continued)

frequency of the rotors, depending on the mechanical strength of the skin tissue; a communication interface.

20 Claims, 5 Drawing Sheets

(51) Int. Cl.

| | |
|---|---|
| ***A61H 9/00*** | (2006.01) |
| ***A61H 15/02*** | (2006.01) |
| ***A61H 23/00*** | (2006.01) |
| ***A61M 37/00*** | (2006.01) |
| *A61B 17/00* | (2006.01) |
| *A61B 50/13* | (2016.01) |

(52) U.S. Cl.

CPC ....... *A61H 15/0085* (2013.01); *A61H 23/006* (2013.01); *A61M 37/0092* (2013.01); *A61B 2017/00199* (2013.01); *A61B 2017/00761* (2013.01); *A61B 2017/00765* (2013.01); *A61B 2017/320069* (2017.08); *A61B 50/13* (2016.02); *A61H 2015/0014* (2013.01); *A61H 2015/005* (2013.01); *A61H 2015/0071* (2013.01); *A61H 2201/0153* (2013.01); *A61H 2201/0207* (2013.01); *A61H 2201/0228* (2013.01); *A61H 2201/105* (2013.01); *A61H 2201/1654* (2013.01); *A61H 2201/169* (2013.01); *A61H 2201/5007* (2013.01); *A61H 2201/5071* (2013.01); *A61H 2201/5092* (2013.01); *A61H 2207/00* (2013.01); *A61H 2230/505* (2013.01)

(56) References Cited

U.S. PATENT DOCUMENTS

| | | | | |
|---|---|---|---|---|
| 2002/0147467 | A1 | 10/2002 | Bernabei | |
| 2005/0261584 | A1 | 11/2005 | Eshel et al. | |
| 2015/0133835 | A1* | 5/2015 | Fadil | A61H 7/001 601/118 |
| 2023/0413979 | A1* | 12/2023 | El-Sherif | A61H 15/02 |

FOREIGN PATENT DOCUMENTS

| | | |
|---|---|---|
| EP | 2 361 598 | 8/2011 |
| GB | 2 303 552 A | 2/1997 |
| IT | UB20161062 | 8/2017 |
| WO | 2007 122656 | 11/2017 |

OTHER PUBLICATIONS

Written Opinion of the ISA for PCT/IB2020/050221 dated Mar. 13, 2020, 11 pages.

* cited by examiner (a)

(b)

INTEGRATED DEVICE FOR THE NON-INVASIVE PERSONALISED TREATMENT OF SKIN BLEMISHES AND ASSOCIATED MULTI-STEP METHOD

This application is the U.S. national phase of International Application No. PCT/IB2020/050221 filed 13 Jan. 2020, which designated the U.S. and claims priority to IT patent application No. 102019000000679 filed 16 Jan. 2019, the entire contents of each of which are hereby incorporated by reference.

BACKGROUND OF THE INVENTION

Field of the Invention

The present invention regards the field of aesthetic and sports medicine as well as rehabilitation. In particular it describes a device suitable to recognize and treat, by means of compressive microvibration, some diseases such as cellulite, tissue recompacting, lymphatic and venous stasis, edematosis, muscle and cicatricial contractures, shoulder-neck syndrome and pubalgias. Other fields of application of this device are pre-post-surgery treatments for athletes, sports massage, lymphatic drainage and the treatment of pains of various origins.

Description of the Related Art

The so-called cellulite, also called "gynoid lipodystrophy", "fibrous oedematous panniculopathy", "adiposis edematosa", "sclerotic fibrous oedematous panniculopathy", "dermopanniculosis deformans", "status protrusions cutis, and "liposclerosis", is a topographical manifestation of the skin associated with depressions or introflections frequent in pelvic and abdominal areas, hips, glutei and thighs. It may also manifest itself associated with nodules in subcutaneous adipose tissue and, in rare cases, with a suspected inflammatory condition.

The great confusion about the name to give to cellulite reflects the difficulty of correctly understanding the nature of the phenomenon. Despite the great interest in the treatment of this condition and the huge market for topical treatments aimed at improving its appearance, cellulite is still an enigmatic condition for medical researchers.

The high incidence (80-90%) in the female population presenting cellulite blemishes in post pubertal age, in addition to the fact that it occurs without symptoms, makes it to be considered a normal physiological condition. It can instead be considered in a pathological framework pointing out that whereas it is true that it is a normal condition for many women, it does not apply to all, and that in its most serious forms it manifests itself with nodules painful to palpation which lead to suspicion of inflammatory processes. Furthermore, it is generally associated with an excessive accumulation of subcutaneous adipose tissue whose relationship with cardiovascular risk is unclear.

Dozens of different causes have been hypothesised, including: metabolism disorders, nutritional disorders, specific subcutaneous architectures, alterations of connective tissue structure, hormonal factors, genetic factors, microcirculatory system disorders, alterations in the lymphatic system, alterations in the extracellular matrix, inflammations.

Cellulite classifications are as follows:

oedematous: i.e. associated with an accumulation of liquids, especially around ankles, calves, thighs and arms.

fibrous: i.e. associated with an increase in trabecular structures and connective tissue septa which divide the subcutaneous adipose tissue into various lobes; fibrous cellulite is characterised by small nodules that are not perceivable to the touch except as a subcutaneous roughness and by the orange peel-like skin.

sclerotic: i.e. associated with a hardening of the tissues associated with large nodules and plaques; this form can be very painful.

Various measures can help prevent cellulite. Some attention in nutrition, constant physical activity, the use of comfortable and not too tight clothes, shoes with not too high heels and changes in posture are the easiest remedies to implement to prevent this annoying disorder. The huge market of treatments for reducing cellulite ranges from topical products to liposuction. However, many of these treatments lack evidence of effectiveness. Below is a list of the most common ones:

topical products i.e. creams and the like to be applied manually on the area in question constantly and on daily basis for long periods of time;

massages;

pressure therapy: treatment based on the external pressure of the patient's limbs or the abdominal area thereof through a specific apparatus;

mesotherapy: a technique for the administration of drugs through the intraepidermal, superficial and deep intradermal and subcutaneous or hypodermic routes, has the advantages of being suitable for reducing doses of active ingredient which have a prolonged effect over time;

emulsion-lipolysis: a pharmacological therapy which can be carried out by means of a regional injection with hypothalamic phospholipids, carnitine, aminophylline, lidocaine 2%, saline solution;

lipoapoptosis: a pharmacological therapy that can be carried out by means of a regional injection with vitamin C, trivalent iron, lidocaine 2%, water for injectable preparations;

carboxytherapy: treatment that originates from thermal medicine and consists in the administration of carbon dioxide through the subcutaneous route;

osmotic lipoclasia: cutaneous biostimulation with platelet-rich plasma;

oxygenoclasia: technique for introducing pure medical oxygen into the excess fat through a small needle;

endermologie system: a technique designed in France in the 70*s* in which a vacuum system and a plurality of rollers, mounted on a handpiece, exert pressure and lifting actions on the skin causing a redistribution of subcutaneous fat.

ultrasound therapy: treatment based on the effect produced by mechanical vibrations applied to the outer tissues of the body by means of an ultrasonic transducer.

laser therapy: treatment that acts at various levels of depth based on the power of the transmitted rays.

diathermy: a practice, without scientific validation, which supports curative properties induced by the increase in the temperature of some non-superficial areas of the body caused by the passage of electric current.

As observable from the list above, which is not exhaustive, the market is saturated with treatments, among which there are some without sure results. Ineffectiveness is often due to the fact that, as explained above, the cause of cellulite and of the disorders it entails remain unclear.

There are also various patents claiming treatments for cellulite care such as US 2002147467 which provides for, first of all, an exfoliating treatment to maximize the absorption of the substances applied to the skin, then the administration of mechanical vibrations associated with electric pulsations in the area in question.

EP 1844750, on the other hand, claims an instrument for aesthetic treatments, therefore not of medical nature, which reduces cellulite through ultrasonic vibrations with a frequency between 25 kHz and 50 kHz.

GB 2303552 discloses a medical apparatus capable of reducing cellulite through ultrasounds at a frequency of about 3.3 MHz reaching a depth of 1.27-2.54 cm from the skin surface without overheating the part.

The worldwide patent, WO2007122656, owned by Fenix S.r.l., a market leader in anti-cellulite and anti-blemishes therapies as well as skin disorders in general, claims a computer-controlled vibratory device, used to treat parts of the body, the whose primary characteristic is to apply massages by inducing mechanical oscillations by means of a plurality of massage elements which are rotatably mounted about their own axis in a roller driven by an electric motor. The rotation of the roller around the shaft thereof is controlled by the operator through an electronic control unit, by selecting a program suitable for the treatment to be carried out. The device described in this patent performs a massage based on the resistance opposed by the muscles located under the adipose layer.

An object of the present invention is to provide a device and a compressive microvibration method customised on the disorders suffered by each patient, which performs four actions synergistically by acting on the vascular system at the microcirculation level, on the lymphatic system, on the tissue re-compaction and on the analgesic effect, thus also entailing a muscular effect. The operation of this device relies on a sensor capable of detecting the type of disorder and a dedicated software that determines the best therapy to be followed case by case.

SUMMARY OF THE INVENTION

According to the present invention, a device is provided and a method of use associated thereto that effectively overcomes the aforementioned drawbacks is described.

Advantageously, the device integrates handpieces to perform different treatments to be modulated depending on the disorder suffered by each patient. The treatment is particularly effective on muscle contractures, cellulite, stretch marks, wrinkles and more. The device comprises a portable console provided, at the upper part, with a plurality of recesses each suitable to house a corresponding handpiece.

The device comprises at least 3 handpieces and possibly a fourth additional handpiece. Said handpieces are the following:

A first handpiece suitable for performing a percussion treatment on the body and/or face of a patient by means of a rotor comprising a plurality of rotating elements installed on a corresponding plurality of semi-axes installed equally spaced on the circumference of a ring nut. The rotor is included in a head of the handpiece, which has an opening protected by an elastic membrane designed to allow the percussion to be carried out, avoiding direct contact between the rotating elements and the patient's epidermis. Included in the handle of the handpiece, consisting of two half-handles suitable to be mutually engaged in this case, is the electric motor which controls the percussion frequency of said rotor. Said first handpiece is therefore advantageously suitable cause a microtrauma at the wrinkle furrow, thus facilitating the natural recovery and therefore a reduction of the wrinkle depth or of the stretch on which the percussion is applied.

Furthermore, in the preferred embodiment said first handpiece has a movable head, tilted according to an angle of 10°, provided with a spot laser and a micro-camera.

A second handpiece suitable for carrying out an ablative micro-vibration treatment on the patient's body, also obtaining an exfoliating effect. This object is achieved by means of a rotor comprising a plurality of rotating and vibrating elements suitable to vibrate and rotate in a converging or diverging direction with respect to a median axis, according to the arrangement of a plurality of pins on which said rotating elements are fitted. The median axis of the rotor is occupied by a middle ring nut on which the operator can advantageously act to cause said rotating elements to impart a converging or diverging force on the patient's skin. The rotor is inserted into a shell provided with an open side, which allows the contact between said rotating elements and the body of said patient, and with a closed side facing the operator, comprising a pair of light indicators suitable to signal the converging or diverging direction of the rotating elements to the operator. The rotor is connected beneath an electric motor, integrated in the handle of the handpiece, which determines the frequency of rotation and vibration of the rotor. Said second handpiece is therefore advantageously suitable to expand or compact the skin tissue by alleviating blemishes such as wrinkles, stretch marks and scars, thus also obtaining an exfoliating effect, referred to as "stretching" in the technical jargon. In the preferred embodiment of the present invention, this exfoliating effect is obtained by a surface treatment of the outer surface of each rotating element which has a predetermined roughness and density, or softness.

A third handpiece suitable for performing a compressive micro-vibration treatment on the face of a patient by means of a rotor provided with rotating elements suitable to vibrate and rotate around a plurality of pins which extend from an upper ring nut to a lower ring nut. The rotor is inserted into a shell provided with an open side, which allows the contact between said rotating elements and the body of the patient, and with a closed side facing the operator, provided with a light pressure indicator which signals, to the operator, the pressure with which he/she is pressing on the patient's face. Also in the case of the third handpiece, the rotor is driven by an electric motor integrated in the handle. Thus, said third handpiece is advantageously suitable to expand the pores of the patient's epidermis.

A fourth handpiece, present only optionally with respect to the device of the invention, suitable for carrying out a treatment for the vibro-transportation of active ingredients in depth on the body and/or face of a patient by means of a vibrating head suitable to vibrate, at a predetermined frequency driven by an electric motor integrated in the handle of the handpiece. Optionally, said fourth handpiece also comprises an active ingredient reservoir suitable to release the desired amount of cream, gel, or mousse on the patient's body upon pressing a special key by the operator. Using the fourth handpiece following the application of at least one of the first three handpieces allows an in-depth penetration of the desired active ingredient, which would otherwise be achievable only by injection, making the treatment non-invasive, painless, and at least equally effective.

All said handpieces are power-supplied by special electrical cables which connect them to said console. They can also be easily disconnected by operating special connection means which connect the distal ends of said power supply cables to the electric motors included in said handpieces.

Each handpiece also advantageously includes a rotation and vibration adjustment device and an electric energy absorption sensor. The latter is suitable to detect the amount of electric energy absorbed by each handpiece in order to obtain the desired rotation and vibration of the corresponding rotors, communicating the detected data to a control unit programmed with a dedicated software. By processing the data coming from said electric energy absorption sensor, the control unit acts, in real time, on the frequency adjustment devices of the handpiece in order to obtain an immediate variation of the rotation and vibration frequency of said rotors, within a pre-established range comprised between 20 Hz and 700 Hz, preferably between 40 Hz and 355 Hz, depending on the mechanical strength provided by the skin tissue of the patient at contact with the handpiece in use.

This device constitutes the main advantage offered by the present invention, given that the operator is greatly facilitated in the work thereof by the possibility of automatically and immediately identifying and modifying the intensity of the treatment in areas affected by different muscle contractures or tissue disorders.

All the data relating to the therapy in progress are displayed and can be modified manually by the operator through a communication interface, preferably integrated in said console. More in detail, the method of use of the device according to the present invention consists of the following steps:

- setting the parameters, through said communication interface, based on the characteristics of the patient's tissue, the age and musculature thereof;
- a test, in which, by gripping a handpiece and placing the relative rotor at contact with the patient's body or face, the relative electric energy absorption sensor sends the detected data to the control unit integrated in the treatment device. By comparing the electric energy absorption data and the data of the vibrations and rotations frequency set by the operator, through the communication interface, the control unit communicates to the operator the correctness or incorrectness of the frequency range of the vibrations and rotations set;
- administering the therapy, in which the operator covers the areas of the patient's body or face to be treated with a handpiece at a time according to a sequence pre-established by the type of treatment. In the preferred embodiment, the recesses in which the handpieces are housed are advantageously provided with means for retaining said handpieces suitable for releasing the handpieces only in the order pre-established by the therapy being carried out. During the treatment, the operator applies a predetermined pressure perpendicular to the skin tissue of the patient and, should the electric energy absorption sensor, possibly combined with a pressure or a motor revolutions sensor, of the handpiece in use, detect an area of greater mechanical strength, for example a muscle contracture, said control unit, which processes the data sent by said electric energy absorption sensor, sends a command to increase the vibrations and rotations frequency to the frequency adjustment device of the handpiece in use, until a lower mechanical resistance is detected.
- At the end of therapy, in a fourth step of monitoring the homogeneity of the treatment on the area affected by the skin disorder or blemish, the operator examines the reddening of the skin due to the vascularization of the tissue induced by the treatment, so as to ensure that each area of the body or face has been treated uniformly. A more scientific version of this final step of the method of use of the machine provides for the presence of a temperature sensor for each handpiece, suitable to communicate, to the control unit of said device, the temperature variation of the skin tissues of the patient from the beginning of the treatment.

Other embodiments of the device which make it even more advantageous both in terms of efficiency and comfort for the operator and the patient, provide for the presence of at least one of the following devices:

- a resistor inside said handpieces, suitable to heat the portion of the handpiece which is at contact with the patient's body or face, up to a predetermined temperature;
- a resistor inside the recesses suitable to heat the corresponding handpieces before they are placed at contact with the patient's body or face;
- a device for disinfecting the handpieces by means of a common infrared lamp.

Lastly, the rotating elements of the handpieces can consist of balls, ovoids or cylinders, preferably balls, arranged honeycomb-like or V-like manner, made of anti-allergy silicone or gel of hardness comprised between 5 shore and 100 shore, preferably 35 shore.

In a variant embodiment of said rotating elements (balls) the effects of the treatment described so far, already very advantageous, are added to the further beneficial effects of the "micro-vacuum" by virtue of the fact that the outer surface of said rotating elements is provided with a plurality of spherical cap-shaped recesses suitable to create a suction effect when pressed onto the patient's epidermis.

The advantages provided by the present invention will be clear in light of the description outlined up to now. Furthermore, they will be more apparent due to the attached figures and relative detailed description.

BRIEF DESCRIPTION OF THE DRAWINGS

The invention will be described hereinafter in at least one preferred embodiment, provided by way of non-limiting example, with reference to the attached figures, wherein:

FIG. 2(*b*) shows, in detail, an exploded view of the rotor 2.11 of the first handpiece 2.

FIG. 3(*b*) shows a three-dimensional view of the rotor 3.10 of the second handpiece 3.

FIG. 3(*c*) shows an exploded view of the aforementioned rotor 3.10.

FIG. 4(*b*) shows an exploded view of the rotor 4.9 of the third handpiece 4.

FIG. 4(*c*) shows an exploded view of the shell 4.4 of the third handpiece 4.

FIG. 4(*d*) shows a three-dimensional view of the aforementioned rotor 4.9.

DESCRIPTION OF THE PREFERRED EMBODIMENTS

Now, the present invention will be illustrated purely by way of non-limiting or non-binding example, with reference to the figures illustrating some embodiments regarding the present inventive concept.

Figure 1:
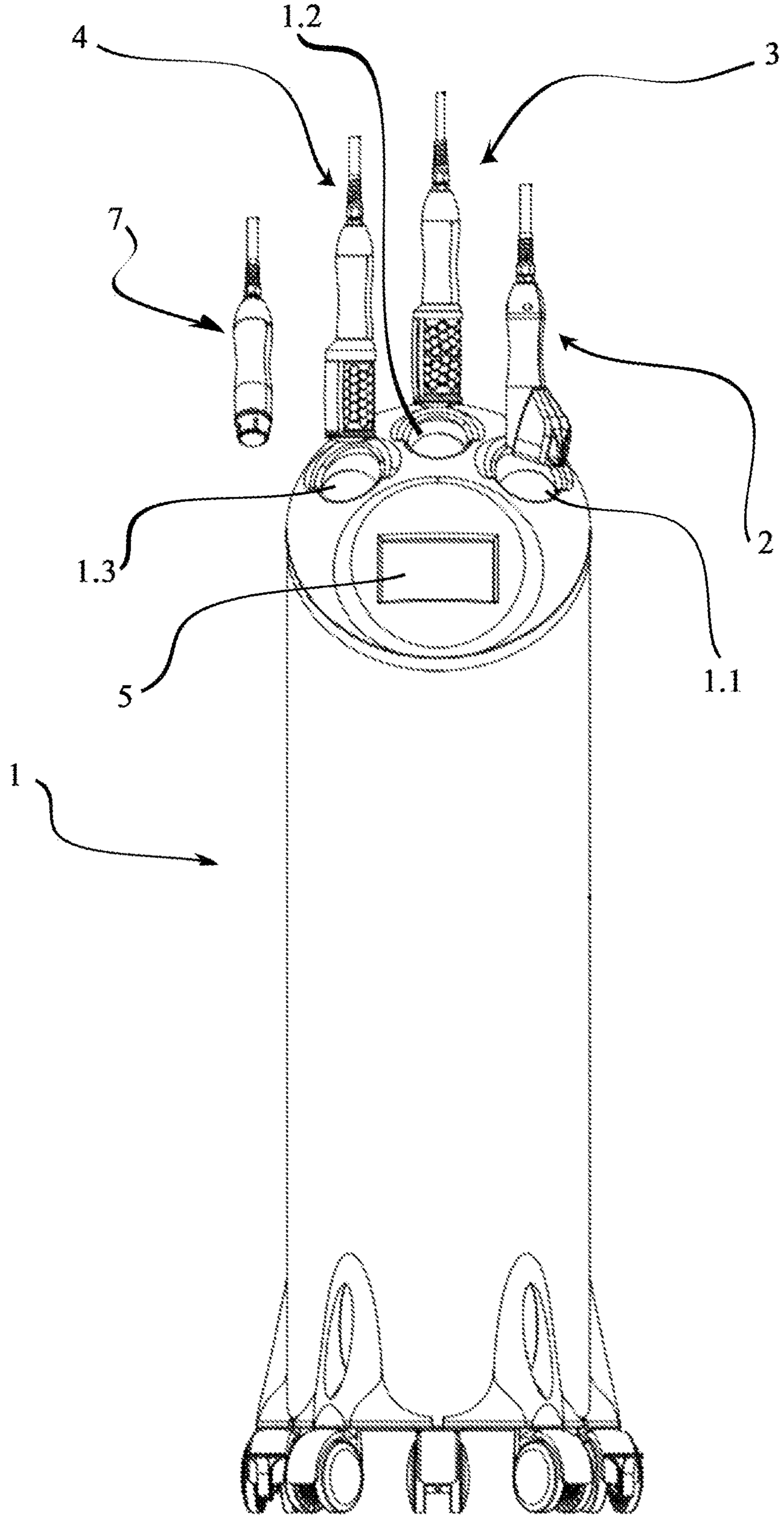
FIG. 1 shows a three-dimensional view of the device in a three-recess embodiment 1.1-1.2-1.3. Also shown is the fourth handpiece 7, optionally present.
Figure 2:
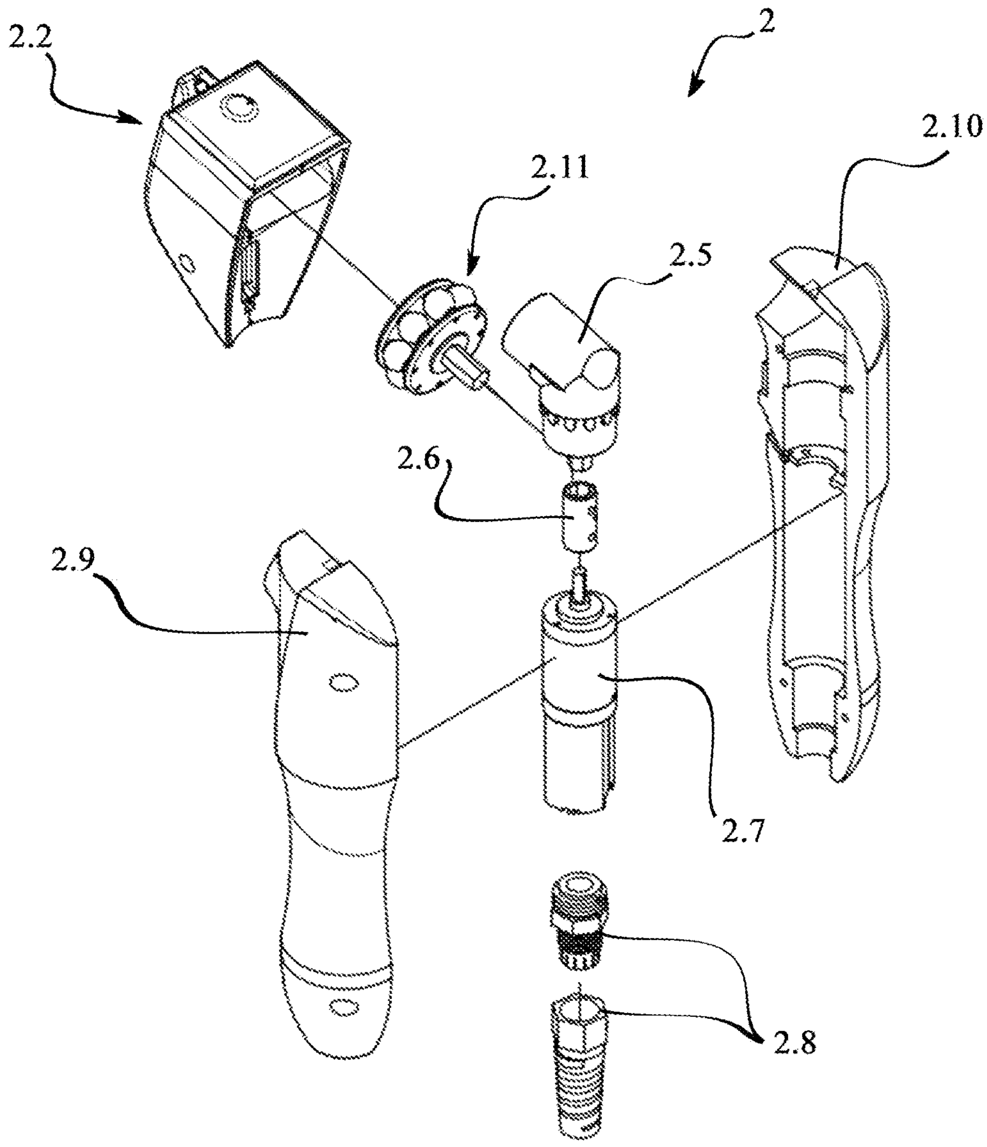
FIG. 2(*a*) illustrates an exploded view of the first handpiece 2.
Figure 2:
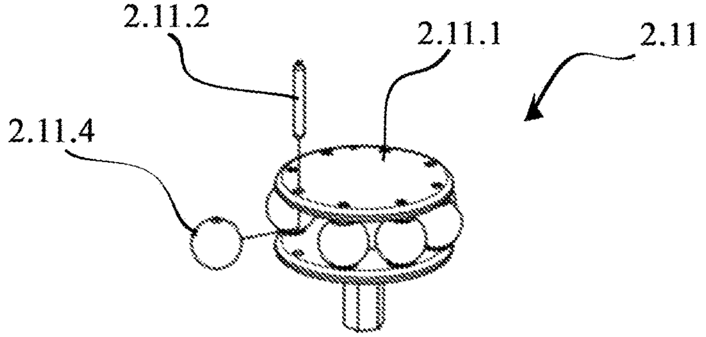
Figure 3:
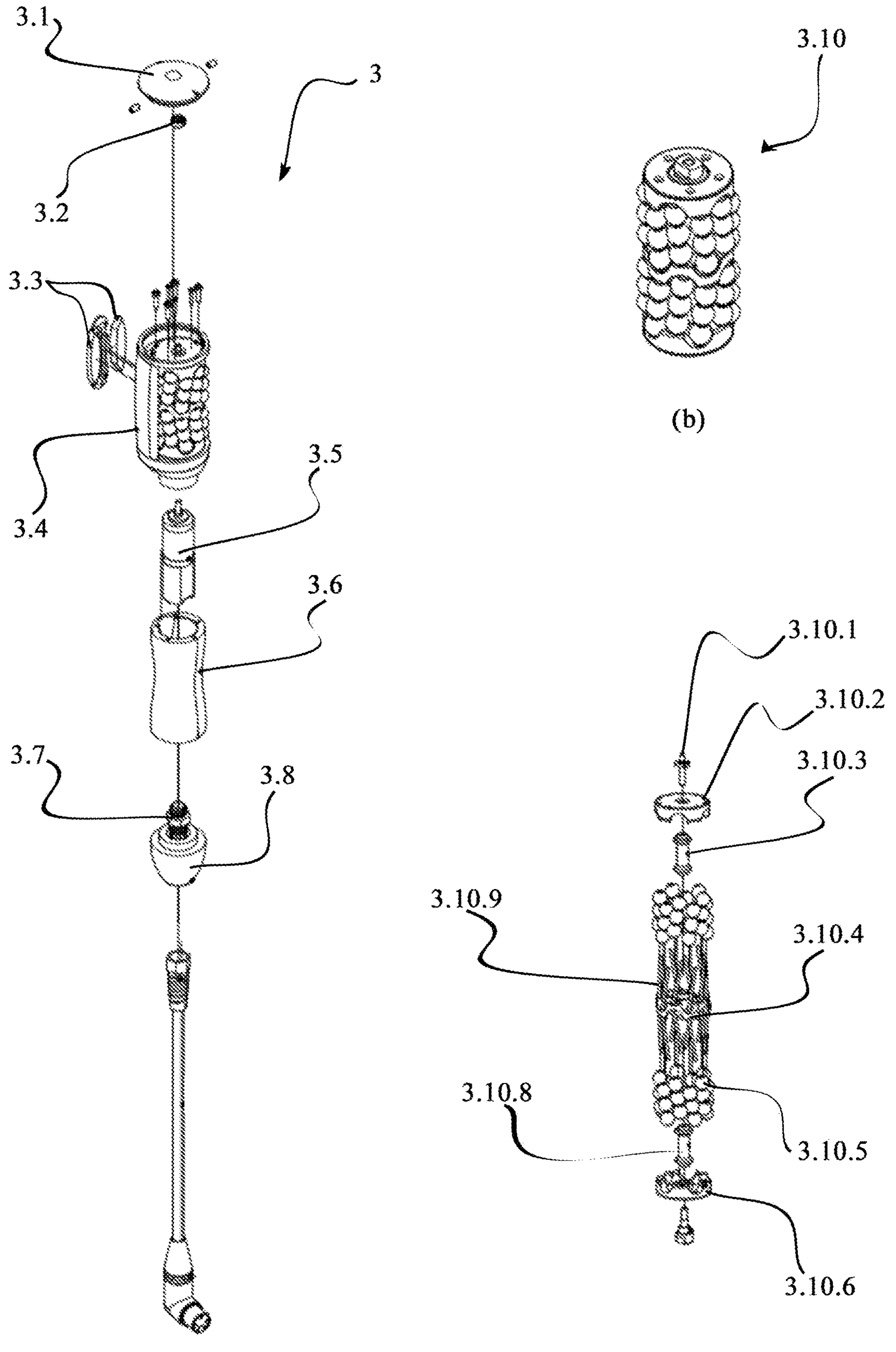
FIG. 3(*a*) shows an exploded view of the second handpiece 2.
Figure 4:
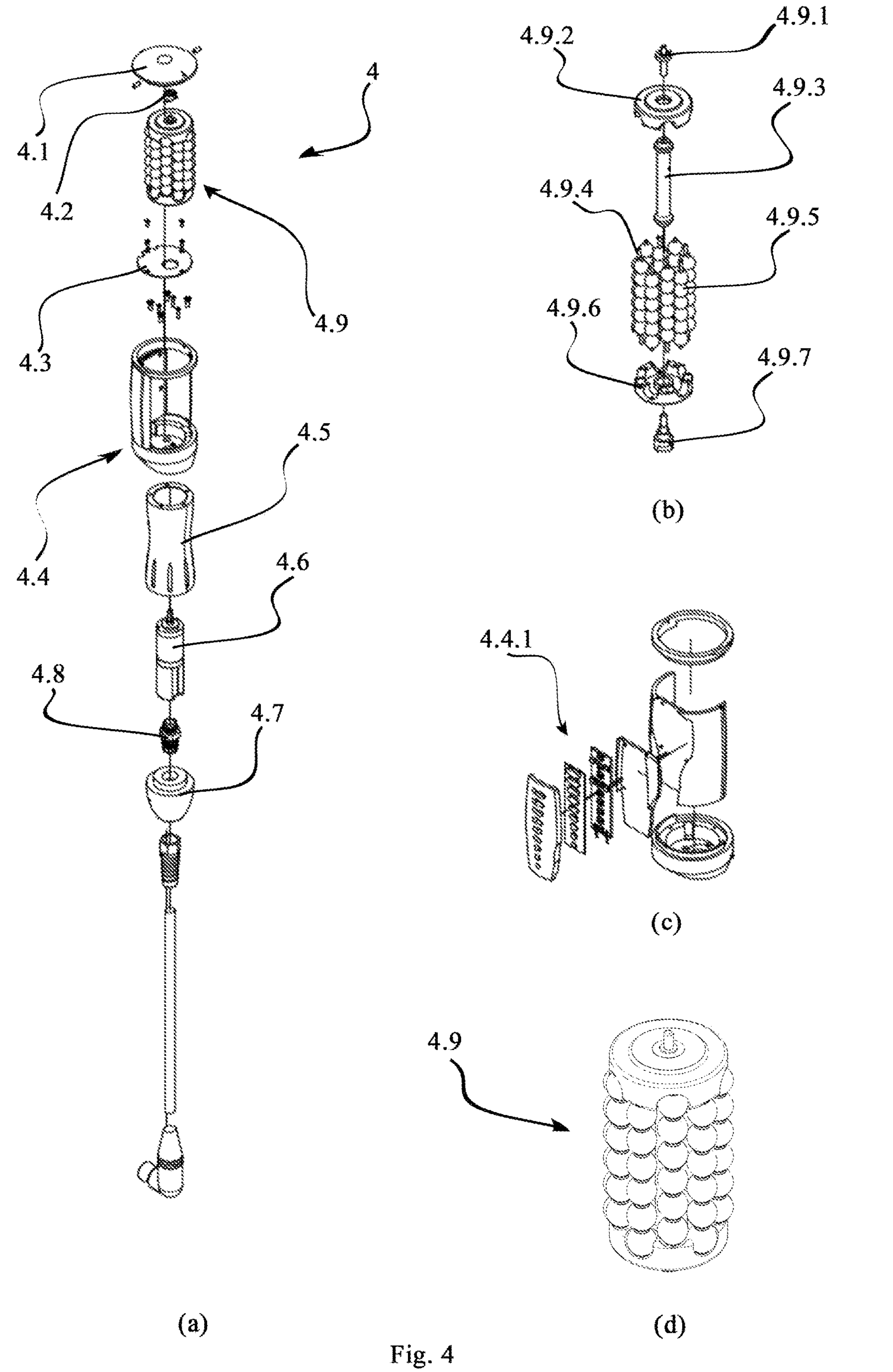
FIG. 4(*a*) illustrates an exploded view of the third handpiece 4.
Figure 5:
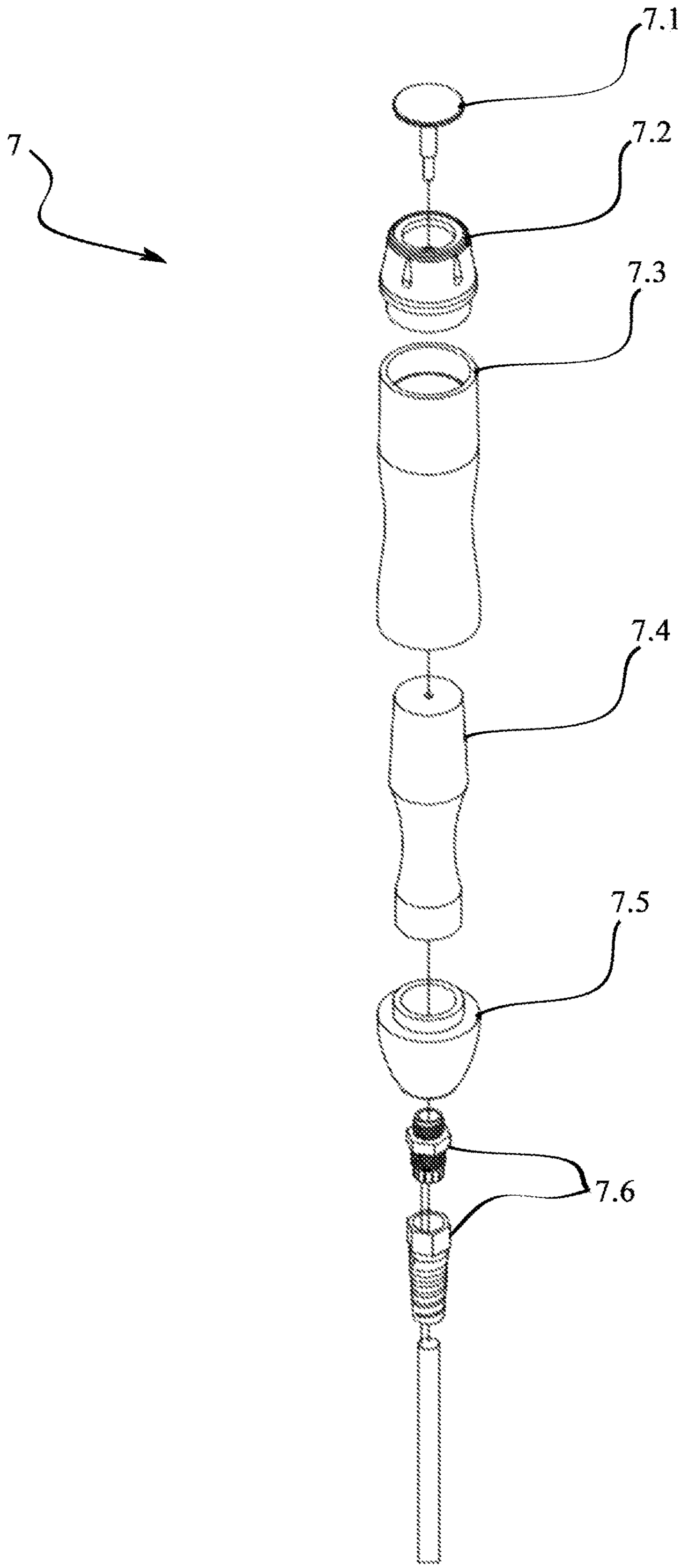
FIG. 5 shows an exploded view of the fourth handpiece 7.

With reference to FIG. 1, shown in its entirety is the device subject of the present invention in which there is a portable console 1 containing a control unit (not visible) provided with a communication interface 5 and with three recesses 1.1-1.2-1.3, preferably heated, each of which is suitable to house a corresponding handpiece 2-3-4.

Depending on the patient's disorder, the operator selects a vibrations and rotations frequency range that the rotors 2.11-3.10-4.9 of the handpieces 2-3-4 will perform when placed on the patient's skin.

The correctness of such range is verified immediately by virtue of the fact that each handpiece 2-3-4 is provided with electric energy absorption sensor which communicates the detected data suitable to detect the amount of electric energy suitable to communicate the detected data to said control unit programmed with a dedicated software suitable to process the data coming from said electric energy absorption sensors, possibly combined with pressure or motor revolutions sensor, and to consequently act, in real time, on the frequency adjustment devices of each handpiece 2-3-4 in order to obtain an immediate variation of the rotation and vibration frequency of said rotors 2.11-3.10-4.9, within a pre-established range comprised between 20 Hz and 700 Hz, preferably between 40 Hz and 355 Hz, depending on the mechanical strength provided by the skin tissue of the patient at contact with one of said handpieces 2-3-4;

Subsequently, the operator can proceed with the therapy by covering the areas of the patient's body or face to be treated with a handpiece 2-3-4 at a time, for a pre-established time interval, applying a predetermined pressure perpendicular to the patient's skin tissue. In the recesses 1.1-1.2-1.3 of the console 1, there are retention means which release the handpieces 2-3-4 only in the order pre-established by the therapy being carried out, preventing any possibility of error.

Each handpiece 2-3-4 has a rotor 2.11-3.10-4.9 consisting of rotating elements 2.11.4-3.10.5-4.9.5 or balls arranged in a honeycomb-like or V-like manner, made of anti-allergy silicone or gel with a hardness equal to 35 shore.

In greater detail, the first handpiece 2 is suitable to perform a percussive treatment on the patient's body and/or face. The balls 2.11.4 of the rotor 2.11 are installed on a corresponding plurality of semi-axes 2.11.2 equally spaced on the circumference of a ring nut 2.11.1. The rotor 2.11 is installed between a movable head which allows the movement of the membrane 2.2 and an angular support 2.5. Said head 2.2 is provided with an elastic membrane suitable to allow the execution of the percussion preventing the direct contact between the balls 2.11.4 and the epidermis of the patient. The angular support 2.5, on the other hand, is fitted, by means of a suitable insert 2.6 on an electric motor 2.7 which controls the percussion frequency of said rotor 2.11, power-supplied by a special cable, connected through common connection means 2.8, connected to said console 1. The angular support 2.5, the insert 2.6, the electric motor 2.7 and the connection means 2.8 are arranged in a pair of half-handles 2.9-2.10, which are suitable to engage each other so as to constitute the grip handle of said first handpiece 2.

The second handpiece 3, is suitable for carrying out an ablative micro-vibration treatment on the patient's body. The balls 3.10.5 of the rotor 3.10 vibrate and rotate in a convergent or divergent direction according to the arrangement of a plurality of pins 3.10.9 into which the balls 3.10.5 are fitted. More in detail, said pins 3.10.9 extend from an upper ring nut 3.10.2 to a middle ring nut 3.10.4 and from said middle ring nut 3.10.4 to a lower ring nut 3.10.6. The rotation of said middle ring nut 3.10.4 by said operator modifies the configuration of said pins 3.10.9 in order to cause the balls 3.10.5 to converge or diverge toward or from said middle ring nut 3.10.4. The rotor 3.10 rotates around an upper semi-axis 3.10.3 and a lower semi-axis 3.10.8 and it is inserted into a shell 3.4 provided with an open side and a closed side. The open side allows contact between the balls 3.10.5 and the patient's body while the closed side is directed toward the operator and comprises a pair of light indicators 3.3 suitable to signal to the operator the converging or diverging direction of the balls 3.10.5 on the patient's body. The rotor 3.10 is connected, at the upper part by means of a pin 3.10.1, to a bearing 3.2 and lastly to an upper plug 3.1 of the second handpiece 3. At the lower part, on the other hand, the rotor 3.10 is connected to an electric motor 3.5, integrated in the handle 3.6, power-supplied by a special cable, connected by common connection means 3.7 included in a lower cap 3.8.

The third handpiece 4, is suitable for carrying out a compressive micro-vibration treatment on the patient's face. The balls 4.9.5 of the rotor 4.9 vibrate and rotate around a plurality of pins 4.9.4 which extend from an upper ring nut 4.9.2 to a lower ring nut 4.9.6. The rotor 4.9 rotates, at a pre-established frequency, around a rotation axis 4.9.3 and it is inserted into a shell 4.4 provided with an open side and a closed side. The open side allows the contact between said balls 4.9.5 and the body of said patient; the closed side is directed toward the operator and it comprises a light pressure indicator 4.4.1 suitable to signal, to the operator, the pressure with which he/she is pressing the handpiece 4 on the patient's face. The rotor 4.9 is connected, at the upper part by means of a pin 4.9.1, to a bearing 4.2 and lastly to an upper cap 4.1, whereas at the lower part it is connected, by means of a joint 4.9.7, to an electric motor 4.6, integrated in a handle 4.5, power-supplied by a special cable connected through common connection means 4.8 included in a lower cap 4.7.

At the end of the treatment, the operator verifies whether each tissue was treated homogeneously by monitoring the increase of skin temperature, due to the vascularization of the tissue induced by the treatment, performed by the control unit which processes the temperature data detected by a temperature sensor of the handpiece 2-3-4 in use.

Lastly, it is clear that the invention described up to now may be subjected to modifications, additions or variants obvious to a man skilled in the art, without departing from the scope of protection outlined by the attached claims.

The invention claimed is:

1. Integrated device for non-invasive personalised treatment of skin blemishes, suitable to be operated by an operator in order to perform a treatment on the body and/or on the face of a patient for the reduction of muscle contractures, cellulite, stretch marks, wrinkles and other blemishes, said device comprising a portable console, provided, at an upper part thereof, with a plurality of recesses each suitable to house a corresponding handpiece suitable to be grasped by said operator in order to perform a step of a pre-established treatment on the body and/or on the face of said patient; said handpieces comprising:

a first handpiece suitable to perform a percussion treatment on the body and/or on the face of a patient by a rotor comprising a first plurality of rotating elements installed on a corresponding plurality of equidistant axes on the circumference of a ring nut; said rotor being installed between a movable head, tilted according to an angle of 10°, provided with spot laser and with micro-camera, and an angular support; said head being provided with an elastic membrane suitable to allow to perform the percussion, avoiding the direct contact between the first plurality of rotating elements and the epidermis of the patient; said angular support being fitted, by a suitable insert, on an electric motor which controls the percussion frequency of said rotor; said electric motor being power supplied by a special cable, connected to said first handpiece by common connection means, connected to said console; said angular support, said insert, said electric motor and said connection means being arranged in a pair of semi-handles suitable to be mutually engaged in order to form the handle for grasping said first handpiece; first handpiece being suitable to cause a micro-trauma at a wrinkle furrow, thus facilitating the natural recovery and hence a reduction of the wrinkle depth;

a second handpiece suitable to perform an ablative micro-vibration treatment on the body of the patient by a rotor comprising a second plurality of rotating elements suitable to vibrate and rotate in a mutually converging or diverging direction depending on the arrangement of a plurality of pins on which said second plurality of rotating elements are fitted; said pins extending from an upper ring nut to a middle ring nut and from said middle ring nut to a lower ring nut; the rotation of said middle ring nut by said operator being suitable to modify the configuration of said pins in order to ensure that said second plurality of rotating elements converge or diverge toward or from said middle ring nut; said rotor being suitable to rotate, at a pre-established frequency, around an upper semi-axis and a lower semi-axis; said rotor being inserted into a shell provided with an open side and with a closed side; said open side allowing the contact between said second plurality of rotating elements and the body of said patient; said closed side being directed toward the operator and comprising a pair of light indicators suitable to signal to the operator the converging or diverging direction of the second plurality of rotating elements on the body of the patient; said rotor being connected, at the top part by a pin, to a bearing and finally to an upper cap of said second handpiece; said rotor being connected, at the lower part, to an electric motor integrated in a handle; said electric motor being suitable to determine the rotation and vibration frequency of said rotor and being power supplied by a special cable, connected to said second handpiece by common connection means included within a lower cap connected to said handle, said power supply cable being connected to said console; said second handpiece being suitable to expand or compact the skin tissue, alleviating blemishes, also obtaining an exfoliating effect called "stretching";

a third handpiece suitable to perform a compressive micro-vibration treatment on the face of a patient by a rotor comprising a third plurality of rotating elements suitable to vibrate and rotate around a plurality of pins on which said third plurality of rotating elements are fitted;

said pins extending from an upper ring nut to a lower ring nut; said rotor being suitable to rotate, at a pre-established frequency, around a rotation axis; said rotor being inserted into a shell provided with an open side and with a closed side; said open side allowing the contact between said third plurality of rotating elements and the body of said patient; said closed side being directed toward the operator and comprising a light pressure indicator suitable to signal to the operator the pressure with which he/she is pressing the handpiece on the face of the patient; said rotor being connected, at the upper part by a pin, to a bearing and finally to an upper cap of said third handpiece; said rotor being connected, at the lower part by a joint, to an electric motor integrated in a handle; said electric motor being suitable to determine the rotation and vibration frequency of said rotor and being power supplied by a special cable, connected to said third handpiece by common connection means included within a lower cap connected to said handle, said power supply cable being connected to said console; said third handpiece being suitable to expand the pores of the epidermis of the patient;

at least one rotation and vibration adjustment device, integrated in each handpiece, suitable to control the frequency of said rotations and vibrations of said rotors of said handpieces;

at least one electric energy absorption sensor for each handpiece, suitable to detect the amount of electric energy absorbed by each handpiece in order to obtain the desired rotation and vibration of the relative rotors; said electric energy absorption sensor being suitable to communicate the detected data to a control unit programmed with a dedicated software suitable to process the data coming from said electric energy absorption sensors and to consequently act, in real time, on said frequency adjustment devices of each handpiece in order to obtain an immediate variation of the rotation and vibration frequency of said rotors, within a pre-established range comprised between 20 Hz and 700 Hz, depending on the mechanical strength provided by the skin tissue of the patient at contact with one of said handpieces;

a communication interface, suitable to allow an operator to receive in real time the information regarding the treatment underway and to set the desired parameters, including the frequency of the vibrations and of the rotations to be administered to the patient through said handpieces.

2. The integrated device for the non-invasive personalised treatment of skin blemishes, according to claim 1, further comprising at least one fourth handpiece suitable to perform a treatment for the vibro-transportation of active ingredients deep into the body and/or on the face of a patient by a head suitable to vibrate by exploiting square-wave electrical pulses, at a pre-established frequency driven by an electric motor inserted into a handle connected, at the upper part, to a support from which said vibrating head projects above; said electric motor being power supplied by a special cable, connected to said fourth handpiece by common connection means included within a lower cap connected to said handle, said power supply cable being connected to said console.

3. The integrated device for the non-invasive personalised treatment of skin blemishes, according to claim 2, wherein said fourth handpiece comprises an active ingredient reservoir suitable to release the desired amount of cream, gel, or mousse on the body of the patient upon pressing a suitable key by said operator.

4. The integrated device for the non-invasive treatment of skin blemishes, personalised according to claim 3, wherein said handpieces are provided with an internal resistor suitable to heat the portion of said handpiece that is at contact with the body or with the face of the patient when said handpiece is in use, up to a pre-established temperature.

5. The integrated device for the non-invasive personalised treatment of skin blemishes, according to claim 3, wherein each recess is provided with an internal resistor suitable to heat the corresponding handpieces before they are placed at contact with the body or with the face of the patient.

6. The integrated device for the non-invasive personalised treatment of skin blemishes, according to claim 3, wherein each handpiece is provided with a temperature sensor suitable to communicate, to the control unit of said device, the temperature variation of the skin tissues of the patient from the start of the treatment, said control communicating the value of said variation by means of said communication interface.

7. Multi-step method for the non-invasive personalised treatment of skin blemishes, performed by an operator by an integrated device according to claim 2, in order to perform a treatment on the body and/or on the face of a patient for the reduction of muscle contractures, cellulite, h marks, wrinkles and other blemishes, said method comprising:

first step of setting the parameters, in which an operator sets, by a communication interface of the treatment device, an admissible frequency range for the rotations and vibrations based on the characteristics of the tissue of the patient, on his/her age and on his/her musculature; the frequency of the vibrations being comprised between 20 Hz and 700 Hz;

second test step, in which, by grasping a handpiece of said treatment device, and placing the relative rotor thereof at contact with the body or with the face of the patient, an electric absorption sensor of said energy handpiece sends the detected data to a control unit integrated in the treatment device; said control unit, comparing the electric energy absorption data and the data of the vibration and rotation frequency set by the operator, communicates by the communication interface the correctness or lack of correctness of the vibration and rotation frequency range set by said operator;

third step of administration of the therapy, in which said operator covers the areas of the body or of the face of the patient to be treated with a handpiece, applying a predetermined pressure perpendicular to the skin tissue of the patient; during said third step of administration of the therapy, if the electric energy absorption sensor of the handpiece in use detected a zone of greater mechanical strength, said control unit that processes the data sent by said electric energy absorption sensor, sends a command to increase the frequency of the vibrations and of the rotations to a frequency adjustment device of the handpiece in use, up to detecting a lower mechanical strength; said handpieces being used by the operator according to a pre-established sequence;

fourth step of monitoring the uniformity of the treatment over the entire area affected by the skin disorder or blemish, said step being suitable to be performed by visual analysis of the skin reddening due the vascularization of the tissue induced by the treatment, by the operator, or said step being suitable to be performed by monitoring the increase of skin temperature, due to the vascularization of the tissue induced by the treatment, performed by the control unit which processes the temperature data detected by the temperature sensor of the handpiece in use;

wherein said third step of administration of the therapy comprises a final step of administration of at least one active ingredient, in form of gel, cream or mousse, by a fourth handpiece.

8. The integrated device for the non-invasive personalised treatment of skin blemishes, according to claim 2, wherein said handpieces are provided with an internal resistor suitable to heat the portion of said handpiece that is at contact with the body or with the face of the patient when said handpiece is in use, up to a pre-established temperature.

9. The integrated device for the non-invasive personalised treatment of skin blemishes, according to claim 2, wherein each recess is provided with an internal resistor suitable to heat the corresponding handpieces before they are placed at contact with the body or with the face of the patient.

10. The integrated device for the non-invasive personalised treatment of skin blemishes, according to claim 2, wherein each handpiece is provided with a temperature sensor suitable to communicate, to the control unit of said device, the temperature variation of the skin tissues of the patient from the start of the treatment, said control unit communicating the value of said variation by means of said communication interface.

11. The integrated device for the non-invasive personalised treatment of skin blemishes, according to claim 2, further comprising means for retaining said handpieces suitable to release the constraint between a recess and the corresponding handpiece only in the order pre-established by the therapy that is being performed.

12. The integrated device for the non-invasive personalised treatment of skin blemishes, according to claim 1, wherein said handpieces are provided with an internal resistor suitable to heat the portion of said handpiece that is at contact with the body or with the face of the patient when said handpiece is in use, up to a pre-established temperature.

13. The integrated device for the non-invasive personalised treatment of skin blemishes, according to claim 12, wherein each handpiece is provided with a temperature sensor suitable to communicate, to the control unit of said device, the temperature variation of the skin tissues of the patient from the start of the treatment, said control unit communicating the value of said variation by said communication interface.

14. The integrated device for the non-invasive personalised treatment of skin blemishes, according to claim 1, wherein each recess is provided with an internal resistor suitable to heat the corresponding handpieces before they are placed at contact with the body or with the face of the patient.

15. The integrated device for the non-invasive personalised treatment of skin blemishes, according to claim 14, wherein each handpiece is provided with a temperature sensor suitable to communicate, to the control unit of said device, the temperature variation of the skin tissues of the patient from the start of the treatment, said control unit communicating the value of said variation by said communication interface.

16. The integrated device for the non-invasive personalised treatment of skin blemishes, according to claim 1, wherein each handpiece is provided with a temperature sensor suitable to communicate, to the control unit of said device, the temperature variation of the skin tissues of the patient from the start of the treatment, said control unit communicating the value of said variation by said communication interface.

17. The integrated device for the non-invasive personalised treatment of skin blemishes, according to claim 1, further comprising means for retaining said handpieces suitable to release the constraint between a recess and the corresponding handpiece only in the order pre-established by the therapy that is being performed.

18. The integrated device for the non-invasive personalised treatment of skin blemishes, according to claim 1, wherein said first, second and third pluralities of rotating elements of said handpieces consist of balls, ovoids or cylinders, arranged to form a honeycomb or V shape; said first, second and third pluralities of rotating elements being made of non-allergenic silicone or of gel with hardness comprised between 5 shore and 100 shore.

19. The integrated device for the non-invasive personalised treatment of skin blemishes, according to claim 1, wherein said first, second and third pluralities of rotating elements of said handpieces have the outer surface provided with a plurality of spherical cap-shaped recesses, suitable to create a suction effect when pressed on the epidermis of the patient; the outer surface of said first, second and third pluralities of rotating elements being provided with a surface treatment suitable to obtain a predetermined surface roughness in order to obtain the desired exfoliating effect on the epidermis of the patient.

20. Multi-step method for the non-invasive personalised treatment of skin blemishes, performed by an operator by an integrated device according to claim 1, in order to perform a treatment on the body and/or on the face of a patient for the reduction of muscle contractures, cellulite, stretch marks, wrinkles and other blemishes, said method comprising:

first step of setting the parameters, in which an operator sets, by a communication interface of the treatment device, an admissible frequency range for the rotations and vibrations based on the characteristics of the tissue of the patient, on his/her age and on his/her musculature; the frequency of the vibrations being comprised between 20 Hz and 700 Hz;

second test step, in which, by grasping a handpiece of said treatment device, and placing the relative rotor thereof at contact with the body or with the face of the patient, an electric energy absorption sensor of said handpiece sends the detected data to a control unit integrated in the treatment device; said control unit, comparing the electric energy absorption data and the data of the vibration and rotation frequency set by the operator, communicates by the communication interface the correctness or lack of correctness of the vibration and rotation frequency range set by said operator;

third step of administration of the therapy, in which said operator covers the areas of the body or of the face of the patient to be treated with a handpiece, applying a predetermined pressure perpendicular to the skin tissue of the patient; during said third step of administration of the therapy, if the electric energy absorption sensor of the handpiece in use detected a zone of greater mechanical strength, said control unit that processes the data sent by said electric energy absorption sensor, sends a command to increase the frequency of the vibrations and of the rotations to a frequency adjustment device of the handpiece in use, up to detecting a lower mechanical strength; said handpieces being used by the operator according to a pre-established sequence;

fourth step of monitoring the uniformity of the treatment over the entire area affected by the skin disorder or blemish, said step being suitable to be performed by visual analysis of the skin reddening due to the vascularization of the tissue induced by the treatment, by the operator, or said step being suitable to be performed by monitoring the increase of skin temperature, due to the vascularization of the tissue induced by the treatment, performed by the control unit which processes the temperature data detected by the temperature sensor of the handpiece in use.

* * * * *